United States Patent
Hsu et al.

(10) Patent No.: US 6,683,060 B2
(45) Date of Patent: Jan. 27, 2004

(54) MATRIX METALLOPROTEINASE AND TUMOR NECROSIS FACTOR INHIBITORS

(75) Inventors: Li-Wei Hsu, Taichung (TW); Su-Chen Chang, Taichung (TW); Jeng-Woei Lee, Yunghe (TW); Pang-Hsi Liu, Pingjen (TW); Hui-Ping Lee, Pingtung (TW); Yi-Ching Chen, Nantou (TW); Chun-Tsun Chen, Changhua (TW)

(73) Assignee: Advanced Gene Technology Corp., Taichung (TW)

( * ) Notice: Subject to any disclaimer, the term of this patent is extended or adjusted under 35 U.S.C. 154(b) by 28 days.

(21) Appl. No.: 10/080,662

(22) Filed: Feb. 25, 2002

(65) Prior Publication Data

US 2003/0162743 A1 Aug. 28, 2003

(51) Int. Cl.$^7$ .................... C08B 37/00; C07H 21/00; A01N 43/00
(52) U.S. Cl. .................... 514/49; 514/50; 424/277.1; 930/144; 536/18.7; 536/22.1
(58) Field of Search .................... 536/18.7, 22.1; 514/50, 49

(56) References Cited

PUBLICATIONS

Robins et al. J. Am. Chem. Soc. (1999), vol. 121, pp. 1425–1433.*
Robins et al. J. Am. Chem. Soc. (1996), vol. 118, pp. 11317–11318.*
Brown, P.D. et al. "Association Between Expression of Activated 72–Kilodalton Gelatinase and Tumor Spread in Non–Small Cell Lung Carcinoma" J. Natl. Cancer. Inst. 85:574–578 (1993).
Davies, B. et al. "Levels of Matrix Metalloproteinases in Bladder Cancer Correlate with Tumor Grade and Invasion" Cancer Res. 53:5365–5369 (1993).
Fieberg, H. et al. "Characterization of Matrix Metalloproteinases in 47 Human Tumor Xenografts with High Expression of MMP2 in Melanomas and Sarcomas" [Abstract No. 3058] Proceedings of the 90$^{th}$ Annual Meeting of the American Association for Cancer Research, Philadelphia, PA. Apr. 10–13, 1999.
Gress, T.M. et al. "Expression and In Situ Localization of Genes Coding for Extracellular Matrix Proteins and Extracellular Matrix Degrading Proteases in Pancreatic Cancer" Int. J. Cancer 62:407–413 (1995).
Johnson, L.J. et al. "Matrix Metalloproteinases" Current Opinion in Chemical Biology 2:466–471 (1998).

Normura, H. et al. "Expression of Membrane Typ–Matrix Metalloproteinase in Human Gastric Carcinomas" Cacer Rs. 55:3263–3266 (1995).
Nuovo, G.J. et al. "Correlation of the In Situ Detection of Polymerase Chain Reaction–Amplified Metalloproteinase Complementary DNA and their Inhibitors with Prognosis in Cervical Carcinoma" Cancer Res. 55:267–275 (1995).
Parsons, S.L. et al. "Matrix Metalloproteinases" Br. J. Surg. 87:160–166 (1997).
Robins, M.J. et al. "Biomimetic Modeling of the Decomposition of 2'–Chloro–2'–deoxynucleotdes by Ribonucleotide Reductases to Give 3(2H)–Furanones Which Can Effect Mechanism–Based Inactivation by Michael–Type Alkylation" Journal of American Chemical Society 118:11317–11318 (1996).
Robins, M.J. et al. "Biomimetic Simulation of Free Radical–Initiated Cascade Reactions Postulated to Occur at the Active Site of Ribonucleotide Reductases" Journal of American Chemical Society 121(7):1425–1433 (1999).

* cited by examiner

Primary Examiner—James O. Wilson
Assistant Examiner—La Tonia M. Fisher
(74) Attorney, Agent, or Firm—Morrison & Foerster LLP

(57) ABSTRACT

The invention discloses methods of treatment and prevention for TNFα-related disorders and MMP-related disorders and compounds useful in such treatments. In particular, the invention dislcoses pharmaceutical compositions comprising a compound of the general formula:

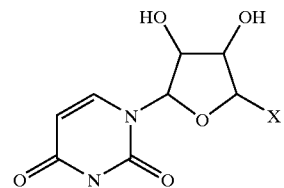

wherein X is a Zn(II) chelating group and selected from the group consisting of $(CH_2)_nOH$, $(CH_2)_nNH_2$, $(CH_2)_nSH$, $(CH_2)_mCOOH$, $(CH_2)_mCOOR$, $(CH_2)_mCONH_2$, $(CH_2)_{m''}CONH-OH$, $(CH_2)_{m''}CONH-R$, and $(CH_2)_nO(PO_3)_{m'''}{}^{(m'''+1)}$, wherein n=2, 3, 4, or 5, n'=2 or 3, m=1, 2, 3, or 4, m'=1, 2, 3, 4, 5, or 6, m''=1, 2, 3, and R=—$C_{m'}$, $H_{2m'+1}$ or aryl groups, especially 1-[3,4-dihydroxy-5-(2-hydroxyethyl)-tetrahydrofuran-2-yl]pyrimidine-2,4(1H,3H)-dione, which has an inhibitory effect on matrix metalloproteinase-2 (gelatinase A) and on the binding of TNFα to TNFα-RI.

5 Claims, 7 Drawing Sheets

MATRIX METALLOPROTEINASE AND TUMOR NECROSIS FACTOR INHIBITORS

FIELD OF THE INVENTION

The present invention relates to novel compounds that are useful in pharmaceutical applications for inhibiting the function of proteins. More specifically, the present invention relates to inhibitors of both of matrix metalloproteinase and tumor necrosis factor.

DESCRIPTION OF RELATED ART

Matrix metalloproteinases (MMPs) is constituted of at least 28 zinc-containing proteolytic enzymes that play an integral role in the physiology of the extracellular matrix (ECM). MMPs play a major role in the degradation of basement membrane and the remodeling of ECM. Certain normal physiological processes such as fetal development, inflammatory cell migration, wound healing and angiogenesis depend on the regulated activity of MMPs and natural tissue inhibitors of metalloproteinases (TIMPs). In pathological processes, such as the development of cancer, tissue-specific MMPs may be recruited to permit primary tumor growth and then the development of metastatic diseases. Activation of these MMPs has been implicated in tissue invasiveness, metastases and angiogenesis. Thus, MMP inhibition offers novel and alternative therapy to current treatment for many different types of cancer (Johnson, L. J., Dyer, R., and Hupe, D. J. Matrix Metalloproteinases. *Current Opinion in Chemical Biology;* 1998.2: 466–471 (1998)).

There are three distinct classes of MMPs divided by their target: collagenases (MMP-1, MMP-8, and MMP-13), stromelysins (MMP-3, MMP-10, MMP-11), and gelatinases (MMP-2 and MMP-9). MMPs are secreted into the ECM in their proenzyme form, which requires activation by other enzymes. One class of the activators is the enzyme membrane type MMP (MT-MMP). The MT-MMPs (MMP-14, MMP-15, MMP-16, MMP-17) have a transmembrane domain and are essential in the activation of pro-MMP.

Among the MMPs as mentioned above, certain MMPs (MMP-2 and MMP-9) are correlated and their over-expression has been evaluated extensively in different kinds of tumors, such colon, gastric, head and neck, prostate, and lung cancer. For example, studies showed that in colorectal cancer, both MMP-2 and MMP-9 (in both their proenzyme and active forms) were over-expressed in cancerous tissue when compared with the normal mucosa. Similar findings had been shown in gastric cancer and pancreatic cancer (Gress T. M., Muller-Pillasch F., Lerch, M. M., et al. Expressioin and in-situ localization of genes coding for extracellular matrix proteins and extracellular matrix degrading proteases in pancreatic cancer. *Int. J. Cancer* 1995, 62:407–413; Normura H, Sato H. Seiki M. et al. Expression of membrane type-matrix metalloproteinase in human gastric cancinomas. *Cancer Res* 1995; 55:3263–3266; Parsons S L, Watson S A, Brown P D, et al. Matrix metalloproteinases. *Br. J. Surg.* 1997, 87: 160–166). Over-expression of MMP-2 and MMP-9 was also correlated with tumor stage, tumor aggressiveness and poor prognosis for gastrointestinal, cervical, bladder and lung tumors (Nuovo G J, MacConnell P B, Simisir A, et al. Correlation of the in situ detection of polymerase chain reaction-amplified metalloproteinase complementary DNA and their inhibitors with prognosis in cervical carcinoma., *Cancer Res.* 1995, 55: 267–275; Davies B, Wasman J, Wasan H, et al.). Levels of matrix metalloproteinases in bladder cancer were correlated with tumor grade and invasion (*Cancer Res.* 1993, 53: 5365–5369; Brown P D, Bloxidge R E, Stuart N S, et al.). Association between expression of activated 72-kilodalton gelatinase and tumor spread in non-small cell lung carcinoma existed (*J. Natl. Cancer Inst.* 1993, 85: 574–578). Although there was clear over-expression of MMP in certain tumors, there was variability of over-expression of MMP in different tumor types. For example, Fieberg, et al. studied expression patterns of MMP-2, MMP-3, and MMP-7 in 47 human tumor xenografts, the result of which showed variable degrees of MMP-2 over-expression with 100% of soft tissue sarcomas, 84% of melanomas, 53% of testicular carcinoma and 26% of bladder cancers that exhibited MMP-2 over-expression (Fieberg H, Klostermeyer A, Schuler J B). Characterization of matrix metalloproteinases in 47 human tumor xenografts who exhibited a high expression level of MMP2 in melanomas and sarcomas (Abstract No. 3058, Proceedings of the 90$^{th}$ Annual Meeting of the American Association for Cancer Research. Apr. 10–13, 1999 Philadelphia (Pa.)). These results suggested that MMP-2 was a reasonable therapeutic target for these tumor.

TNFα (tumor necrosis factor-α) plays an important role in the host defense. It causes resistance to many pathogenic microorganisms and some viruses. Even if TNFα has undoubtedly a beneficial function in the activation of host defense, its unregulated production (mainly on the systematic level) could lead to pathological consequences. TNFα plays a significant role in the pathogenesis of septic shock, characterized by hypotension and multiple organ failure among others. TNFα is the main mediator of cachexia characterized by abnormal weight-loss of cancer patients. Often TNFα is detected in the synovial fluid of patients suffering from arthritis. There was a broad spectrum of diseases, where TNFα could play a role. Compounds inhibiting the release of TNFα may be therefore useful in the treatment of numerous pathologies in which TNFα is involved, such as rheumatoid arthritis, Crohn's disease, plaque sclerosis, septic shock, cancer or cachexia associated with an immunodeficiency.

SUMMARY OF THE INVENTION

One objective of the present invention is to provide a compound, 1-[3,4-dihydroxy-5-(2-hydroxyethyl)-tetrahydrofuran-2-yl]pyrimidine-2,4(1H,3H)-dione, which exhibits an inhibitory effect on matrix metalloproteinase-2 (gelatinase A) and on the binding of TNFα to TNFα-RI.

Another objective of the present invention is to provide a compound having a general formula (I) for inhibiting gelatinase A

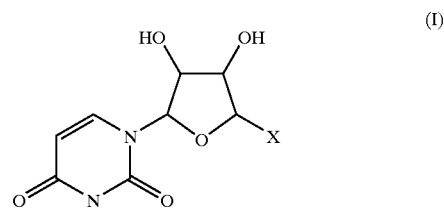

wherein X is a Zn(II) chelating group and selected from the group consisting of $(CH_2)_nOH$, $(CH_2)_nNH_2$, $(CH_2)_nSH$, $(CH_2)_mCOOH$, $(CH_2)_mCOOR$, $(CH_2)_mCONH_2$, $(CH_2)_{m''}CONH-OH$, $(CH_2)_{m''}CONH-R$, and $(CH_2)_{n'}O(PO_3)_{m''}^{(m'''+1)}$, wherein n=2, 3, 4, or 5, n'=2 or 3, m=1, 2, 3, or 4, m'=1, 2, 3, 4, 5, or 6, m"=1, 2, 3, and R=—$C_mH_{2m'+1}$ or aryl groups.

It should be understood that both the foregoing general description and the following detailed description are intended to provide an explanation of the invention as claimed, rather than to limit the scope of the present invention.

BRIEF DESCRIPTION OF THE DRAWINGS

The accompanying drawings are to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
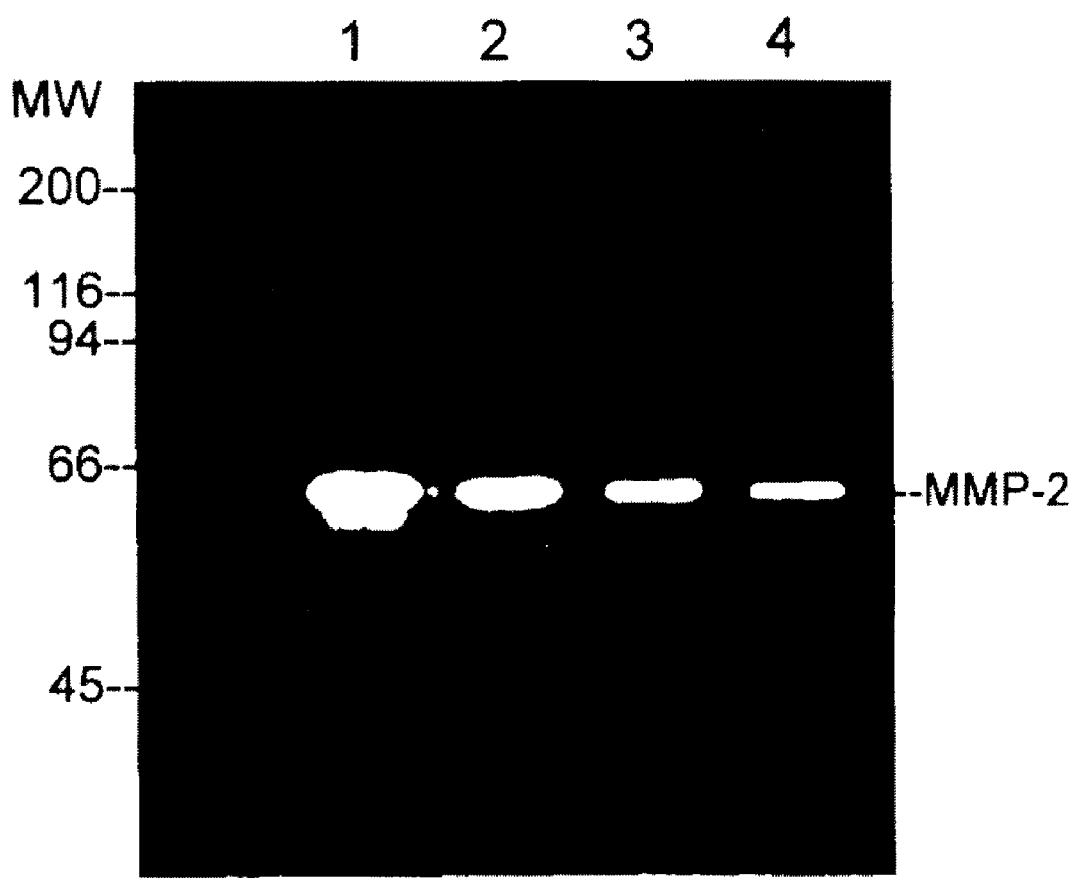
FIG. 1 shows MMP-2 samples analyzed for gelatin degradation activity by zymography stained with Commassie Brilliant Blue R-250.

Reference will now be made in detail to the present preferred embodiments of the invention, examples of which are illustrated in the accompanying drawings. Wherever possible, the same reference numbers are used in the drawings and the description to refer to the same or like parts.

MMP-2 Purification

The MMP-2 enzyme was obtained from cancer cells and then purified by using gelatin-Sephose 4B (Pharmacia). Serum-free conditioned medium from human ovarian carcinoma cells, ES-2, was concentrated 50-fold and then MMP-2 enzyme was obtained by ultrafiltration using a 30,000 MW (molecular weight) cut-off membrane (YM-30, Amicon). The affinity matrix was equilibrated with an equilibration buffer, which was composed of 50 mM Tris.HCl (pH7.6), 10 mM EDTA and 0.01% Tween 20, containing 0.5 M NaCl. After extensive washing with the equilibration buffer containing 0.5 M NaCl, the bound enzyme was eluted with the equilibration buffer containing 1 M NaCl.

In FIG. 1, a gelatin zymography of MMP-2 samples was shown. 0.1% gelatin (Type B, J. T. Baker) was mixed with a 10% polyacrylamide as described (Deryugina, E. I., Bourdon, M. A., Reisfeld, R. A., and Strongin, A., Remodeling of collagen matrix by human cancer cells requires activation and cell surface association of matrix metalloproteinase-2, *Cancer Res.* 58:3734–3750 (1998)) to prepare the gel for electrophoresis. MMP-2 samples were mixed with the SDS/PAGE sample buffer without a reducing agent and then subjected to electrophoretic analysis at 4–8° C. Negative staining with Commassie Brilliant Blue R-250 revealed the enzyme activity on the gel in FIG. 1. The arrow indicated the electrophoretic mobility of active MMP-2. Molecular mass markers were indicated on the left. The amounts on the gel for lanes 1, 2, 3, and 4 were 5 ng, 2.5 ng, 1.25 ng, and 0.63 ng, respectively. The MMP-2 enzyme was then stored in aliquots containing 50% glycerol at −70° C. The MMP-2 samples were also analyzed by Western blotting (data not shown) using a specific monoclonal MMP-2 antibody (NeoMarkers).

The purified enzyme was already an active form with a molecular weight of about 64K. Therefore, an activation process such as using p-aminophenylmercuric acetate (APMA) for the MMP-2 was not required.

Biotinylation of Gelatin

Gelatin was dissolved to a concentration of 2 mg/ml in 20 mM PBS (phosphate buffer solution, pH 7.2). Biotinylation reagent, biotinamidocaproate N-hydroxysuccinimide ester (Sigma) in DMSO as stock, was added to the gelatin at the final concentration of 100 μg/ml. The mixture was incubated at room temperature for 30 min. The excess biotin ester was then exhaustively removed by dialyzing against double distilled water for 2 hours and then against PBS. The concentration of biotinylated gelatin (BG) was determined by using the BCA protein assay reagent (Bio-Rad), and the unmodified gelatin was used as a standard. BG was stored in aliquots containing 0.05% sodium azide at 4° C.

Gelatinase Assay on Microtiter Plates

The gelatinase activity of MMP-2 samples can be revealed by the procedure as described below. In the first part of the procedure, Strapavidin (SA, Sigma) of a concentration of 32 ng/ml in a 50 mM carbonate buffer (pH 9.5) was coated onto 96-well (50 μl/well) C-bottom microtiter plates at 4° C. overnight. The plates were then washed three times with TBST solution, which was composed of 50 mM Tris.HCl (pH 7.35) containing 150 mM NaCl and 0.05% Tween 20, to remove the excessive SA. Following a 2-hour blocking of the SA at 37° C. with 0.5% BSA (bovine serum albumin), the plates were extensively washed three times with TBST solution to remove the excessive BSA.

In the second part of the procedure, The MMP-2 sample was appropriately diluted in TTC solution, which was composed of 50mM Tris.HCl, 1 mM $CaCl_2$, and 0.05% Triton X100 buffer (pH 7.5) and then mixed with equal volume of 400 ng/ml BG in the TTC buffer in the plates. The mixture solution of MMP-2 and BG was incubated at 37° C. for 60 minutes to allow degradation of BG by MMP-2 and binding of the degraded or intact BG to binding sites of the SA. The reaction was stopped by adding and washing the plates four times with TBST.

In the third part of the procedure, the plates were then incubated with diluted Extravidin-Peroxidase (EV-P, 1/5000 in TBST) for 60 min at 37° C. to allow binding of the EV-P to binding sites of the BG. The amount of the diluted EV-P added was 50 μl per well. After extensively washing the plates four times with TBST, the EV-P activity was revealed with 100 μl/well of TMB (3,3',5,5'-tetramehylbenzezidine, a substrate of the EV-P) for 30 min. The reaction was quenched by adding 25 μl/well of 2 M $H_2SO_4$.

Figure 2:
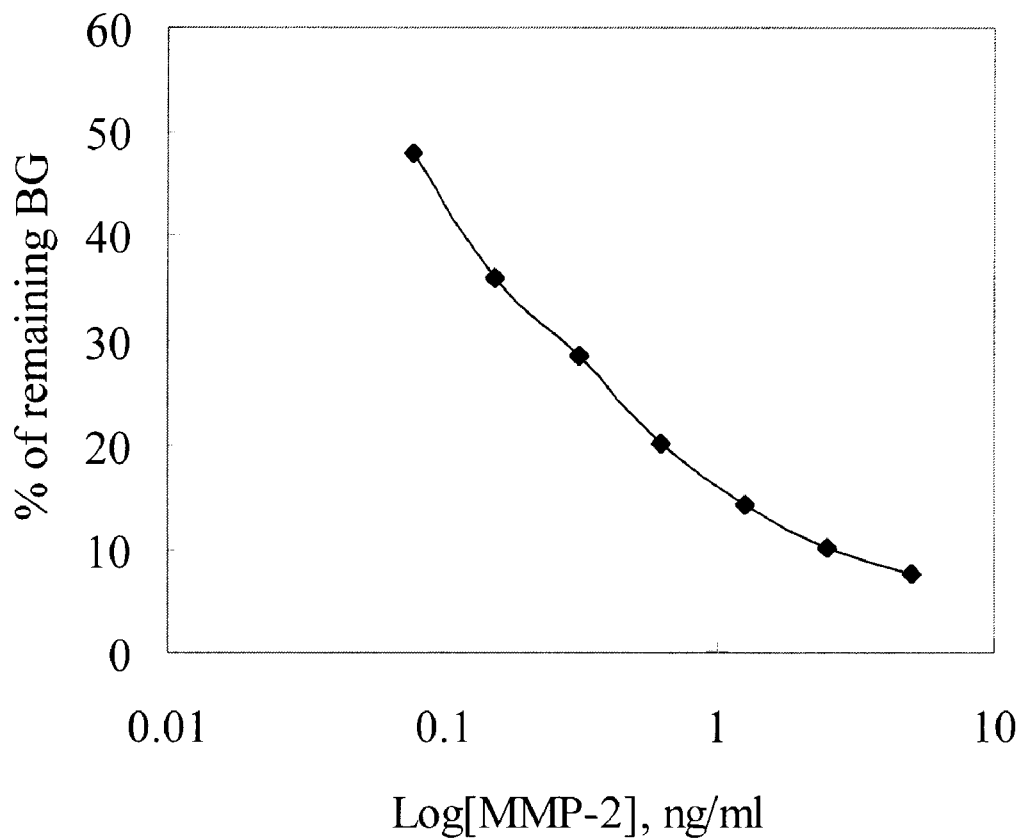
FIG. 2 shows hydrolysis of BG by increasing concentration of the purified MMP-2.

The plates were then read at 450 nm (reference length 470 nm) in a microtiter plate reader (Dynex, MRX). The absorbance at 450 nm increased as the concentration of MMP-2 increased. That is, an increase in the concentration of purified MMP-2 could result in an increase in the hydrolysis of BG, as shown in FIG. 2. In FIG. 2, each data point represented the mean value of a triplicate measurement. The response was linear from 0.078–5 ng/ml of MMP-2 enzyme. Therefore, in the reaction of BG with MMP-2, the absorbance should be a factor 3–5 times lower than an absorbance reading of BG without MMP-2 enzyme (a gelatinase).

Screening for MMP-2 Inhibitor on Microtiter Plates

The inhibition activity of MMP-2 inhibitor can also be revealed by the same procedure as described in the section, GELATINASE ASSAY ON MICROTITER PLATES, except for the second part of the procedure.

To perform the screening for MMP-2 inhibitor screening, the inhibitor candidates were first dissolved in 10% ethanol to allow a final ethanol concentration less than 3%. In the second part of the procedure, the inhibitor candidate (20 μl) was mixed with MMP-2 (30 μl, 150 ng/ml in TTC solution) to allow incubation for 10 min at 37° C. with shaking. The diluted BG (50 μl, 400 ng/ml in TTC solution) was then added to the mixture for each well. Followed by incubation at 37° C. for another 60 min. with shaking, the reaction was stopped by adding and washing four times with TBST solution. The other parts of the procedures were the same as above.

Finding Inhibitors Of MMP-2 From Herbal Extract

The possible MMP-2 inhibitor candidates were found from herbal ingredients fractionalized by HPLC from herb extract. After the collected herbs were washed and dried, methanol was added to the weighed herb (10/1, v/w) to extract the herbal ingredients. The extraction procedure, including blending the mixture and pooling the supernatant after centrifugation at 8000 rpm for 30 minutes, was repeated two times. The supernatant was collected and concentrated with a rotatory evaporator (Heidolph, Laborota 4000) until the final volume was reduced to about 50 ml.

Then a separation procedure was performed. 100 μl of the concentrated supernatant (i.e. the herb extract) was applied to a pre-equilibrated HPLC system (Shimadu). A TSK Gel 80™ reverse phase column (TOSOH) was used for separation. The solvents used for separation were double distilled water and absolute ethanol under 0–100% gradient for 96 minutes at a flow rate of 0.75 ml/min.

One-minute fractions were collected and dried using a SpeedVac (Savant). Each fraction was re-dissolved in 100 μl 10% ethanol for screening for MMP-2 inhibitors. The fraction(s) with MMP-2 inhibitor activity were then further purified by HPLC until the purity was more than 95%.

Figure 3A:
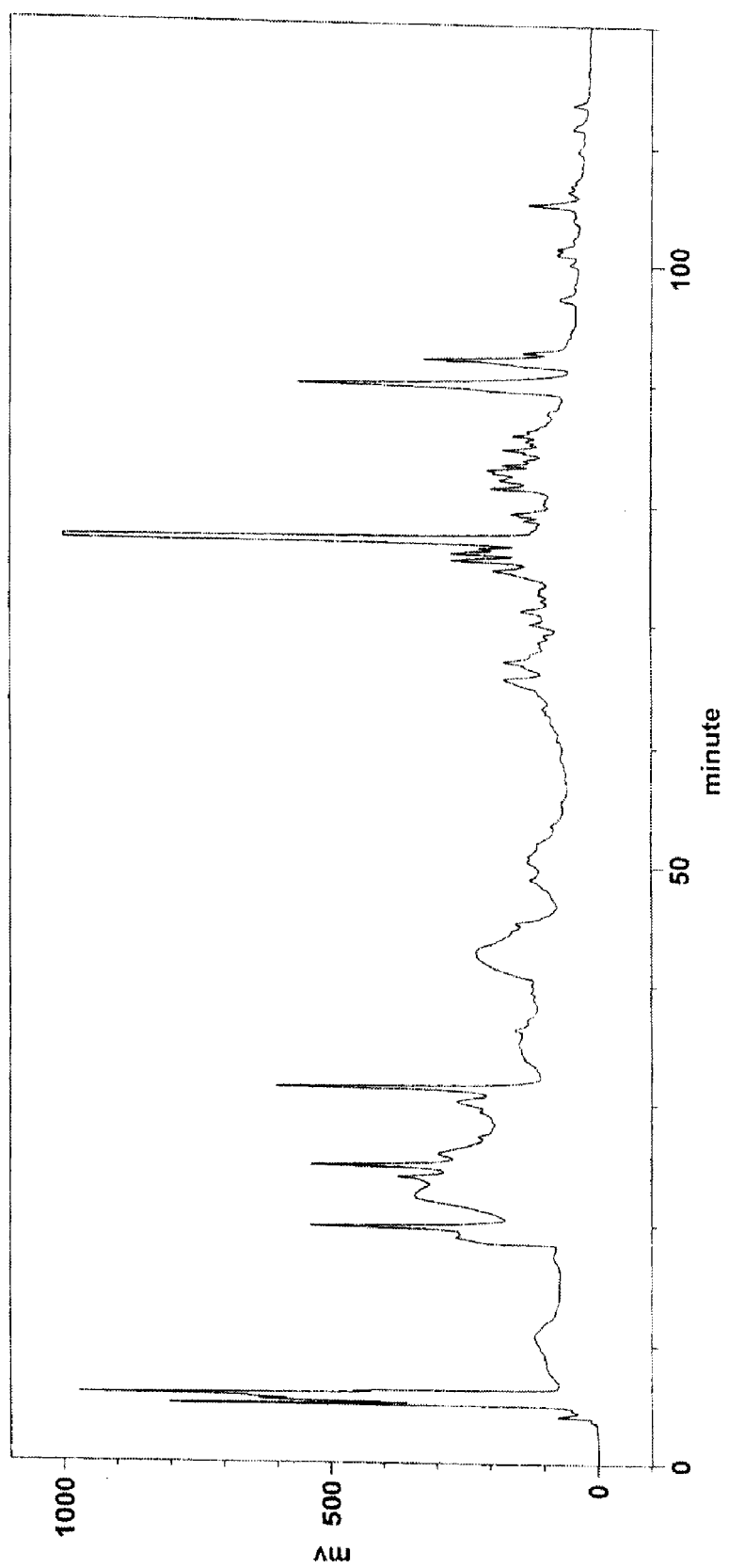
FIG. 3A is a chromatogram of the crude methanol extract of *Taraxacum mongolicum* on a TSK Gel ODS 80™ (TOSOH) reverse phase column (25 cm×4.6 mm) filled with 5 μm gel.

A compound having MMP-2 inhibitory activity was found in the methanol extract of *Taraxacum mongolicum* by using the procedures described above. In FIG. 3A, a chromatogram of the crude methanol extract of *Taraxacum mongolicum* was shown. The crude methanol extract of *Taraxacum mongolicum* was fractionated on a TSK Gel ODS 80™ (TOSOH) reverse phase column. The particle size of the gel in this column was 5 μm, and the column size was 25 cm×4.6 mm. The mobile phase used was a mixture of H2O (A) and absolute ethanol (B, Merck) at a flow rate of 0.75 ml/min. The column was sequentially eluted as follows: 0% B for the first 5 min; a linear gradient of 0–30% B for the next 55 minutes; 30–70% B for the next 20 minutes; 70–100% B for the next 35 min; 100% B for the next 10 minutes; and 100–0% B for the next 1 minute. The detection was performed at a wavelength of 254 nm with a detection sensitivity of 0.01 AUFS.

Figure 3B:
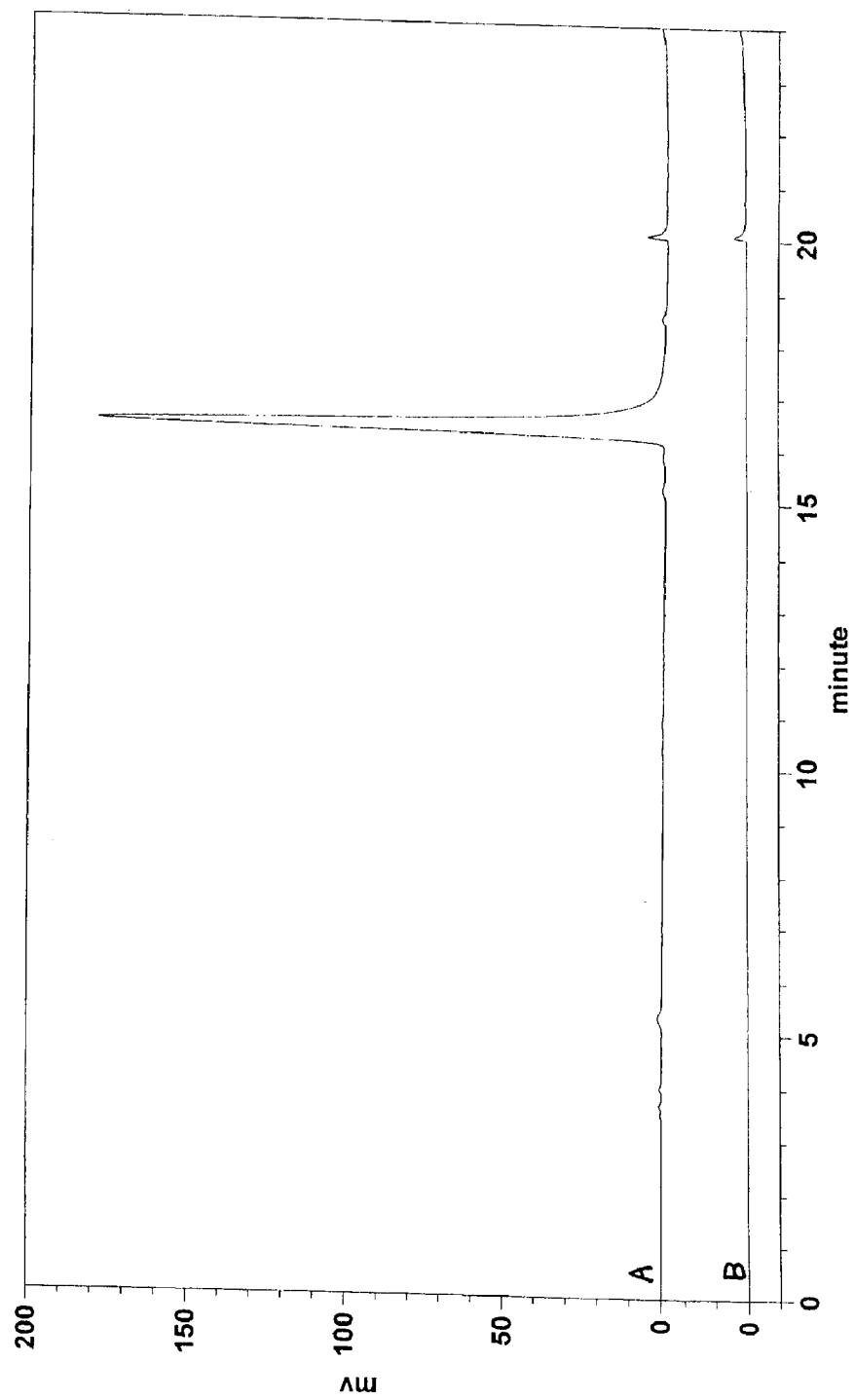
FIG. 3B shows a chromatogram of 1-[3,4-dihydroxy-5-(2-hydroxyethyl)tetrahydrofuran-2-yl]pyrimidine-2,4(1H, 3H)-dione (Compound 1, 1.5 μg) purified from methanolic extract of *Taraxacum mongolicum* on a TSK Gel ODS 80™ (TOSOH) reverse phase column (25 cm×4.6 mm) filled with 5 μm of the gel particle.

In FIG. 3B, a chromatogram of fractions, which was 1.5 μg, with MMP-2 inhibitor activity purified from methanol extract of *Taraxacum mongolicum* was shown. The fractions with MMP-2 inhibitor activity were purified on a TSK Gel ODS 80™ (TOSOH) reverse phase column. The particle size of the gel in this column was 5 μm, and the column size was 25 cm×4.6 mm. The mobile phase used was a mixture of $H_2O$ (A) and absolute ethanol (B,Merck) at a flow rate of 0.75 ml/min. The column was sequentially eluted by a linear gradient of 0–2% B for 12 minutes, 2–100% B for the next 8 minutes, 100% B for the next 5 minutes, and 100–0% B for the next 1 minute. The elution curve of the fractions with MMP-2 inhibitor activity is shown as Curve A, whereas the column eluted by the same blanket eluent is shown as Curve B. The detection was performed at a wavelength of 260 nm with a detection sensitivity of 0.01 AUFS.

The purified active MMP-2 inhibitor was identified as 1-[3,4-dihydroxy-5-(2-hydroxyethyl) tetrahydrofuran-2-yl] pyrimidine-2,4(1H,3H)-dione (which is abbreviated as Compound 1 in other descriptions of this specification) by mass spectrometry (Finnigan Trace MS), FT-IR (Shimadzu, FTIR-8400), ID NMR (Bruker 300 MHz, $^{13}C$ NMR δ(ppm)=166.2(C-7), 152.4(C-9), 142.7(C-11), 102.6(C-10), 90.6(C-5), 86.3(C-2), 75.7(C-4), 71.3(C-3), 62.2(C-15), and 49.4(C-14); $^1H$ NMR δ(ppm)=8.02(1H, d, H-11), 5.90(1H, d, H-2), 5.70(1H, d, H-10), 4.18(1H, m, H-3), 4.15(1H, m, H-4), 4.00(1H, m, H-5), 3.72(2H, m, H-15) and 2D NMR (Varian Inova-600 MHz), and its molecular weight was 258.

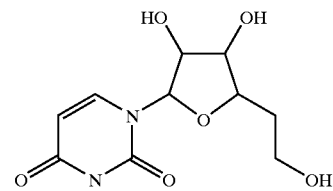

Compound 1

Inhibition of Compound 1 On MMP-2 Activity

The effect of Compound 1 on MMP-2 activity was measured by basically the same procedure as described in the section, GELATINASE ASSAY ON MICROTITER PLATES. As Compound 1 was similar to uridine in chemical structure, the effect of a commercial available uridine (Sigma, U-3750, D-Ribose) on MMP-2 activity was also measured for comparison in the experiment.

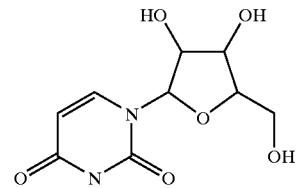

Uridine

Briefly, the 96-well C-bottom microtiter plate was coated with strapavidin (SA) at a concentration of 32 ng/ml in 50 mM carbonate buffer (pH 9.5) at 4° C. overnight. Followed by washing 3 times with TBST, the plate was blocked with 0.5% BSA for 60 minutes at 37° C.

Compound 1 dissolved in $H_2O$ was diluted with TTC to 1 mM. The Compound 1 solution was then further serially diluted to different concentrations. MMP-2 was then added to the Compound 1 solution with different concentrations at a concentration of 0.6 ng/ml by the volume ratio of 3:2. After the mixture was incubated at 37° C. for 10 minutes with shaking at 500 rpm, 50 µl of BG (400 ng/ml in TTC solution) was added to the MMP-2/Compound 1 mixture. Followed by incubation at 37° C. for another 1 hour, the mixture was then transferred into the SA coated plate at a volume of 50 µl/well. After the reaction was allowed to proceed for 1 hour, the plate was then washed 4 times with TBST solution.

EV-P (1/5000 in TBST, 50 µl/well) was added to the plate and incubated at 37° C. for another 1 hour. After extensive washing 4 times with TBST, the EV-P activity was revealed with 100 µl/well of TMB for 30 min. The reaction was stopped by adding 25 µl/well of 2 M $H_2SO_4$. The plates were then read at 450 nm (reference length 470 nm) in a microtiter plate reader (Dynex, MRX).

Figure 4:
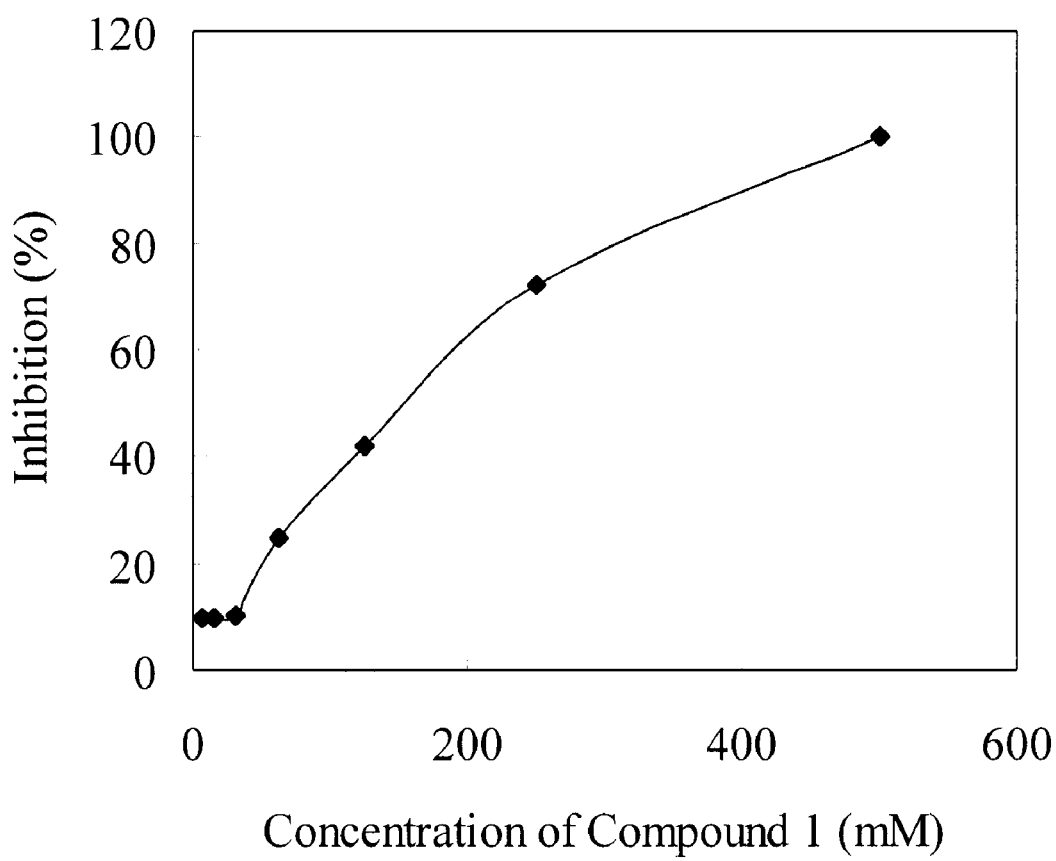
FIG. 4 shows the inhibitory effect of Compound 1 on MMP-2 activity.

The result revealed that Compound 1 caused a dose response inhibition on MMP-2 activity as shown in FIG. 4. In particular, the 50% inhibitory dose (IC50) calculated was 150 µM. However, uridine showed no inhibitory activity to MMP-2 at the concentration of 0.82 mM (data not shown).

Cancer Cell Lines Used for Proliferation/Cytotoxicity Assay

Five cancer-derived cell lines obtained from the American Type Culture Collection (ATCC) were used for the following proliferation/cytotoxicity assay. These cell lines are listed as follow:

ES-2 is a human ovarian carcinoma. It was maintained in a modified McCoy's 5A medium (Gibco) and supplemented with 10% FBS (fetal bovine serum).

COLO205 is a human colon cancer-derived cell line. It was maintained in a RPMI 1640 medium (Hyclone), and supplemented with 10% heat-inactivated FBS.

PC-3 is a human prostate cancer-derived cell line. It was maintained in a Ham's F12 K medium (Gibco) and supplemented with 7% FBS.

A375 is a human malignant melanoma-derived cell line. It was maintained in a Dulbecco's modified Eagle's medium (DMEM, Hyclone) and supplemented with 10% FBS, 4 mM L-glutamine, 4.5 g/l glucose, and 1.0 mM sodium pyruvate.

A549 is a human lung cancer-derived cell line. It was maintained in a F12K medium (Gibco) and supplemented with 10% FBS.

Effect of Compound 1 on Cancer Cell Proliferation In Vitro

To determine the cytotoxicity of Compound 1 or uridine on each cancer cell lines, ES-2, COLO205, PC-3, A375, and A549 cell lines were used. Each cancer cell line at a concentration of $1 \times 10^4$ cells/100 µl in each well (Falcon, MicroTest™ 96) was exposed to Compound 1, uridine or 1 µM paclitaxel (taxol, Sigma) for 72 hours in a complete medium. The Compound 1 and uridine were serially two-fold diluted from the concentration of 0.258 mg/ml.

Cellular viability was estimated by the tetrazolium dye reduction assay (XTT assay, Boehringer Mannheim). The amount of XTT reagent (a tetrazolium salt) added to the bottom wells was 100 µl/well and its concentration was 1 mg/ml. The wells were incubated for 4 hours to allow viable cells to develop color. Absorbance (O.D.) was measured at 450 nm with the reference wavelength at 690 nm.

Due to the aggressive proliferation capacity of cancer cells, it was assumed that viable cells were actively prolif-erating. It was found that Compound 1 and uridine did not reduce cellular viability. Hence, Compound 1 and uridine did not inhibit cell proliferation in vivo (data not shown). However, inhibition of cell proliferation was proportional to the concentration of paclitaxel, but varied from cell line to cell line.

Effect of Compound 1 on Invasive/Metastatic Potential of Cancer Cells

In this method, Boyden chemotaxis assay chambers (Costar Transwell plates) were used. Each Boyden chemotaxis assay chamber included a top chamber having a filter as the bottom side of the top chamber and a bottom well surrounding the top chamber. The bottom side of the top chamber used here was an 8 µm-pore polycarbonate filter.

0.35 ml of a medium with complete nutrition supplements as a chemo-attractant was added to each bottom well. Cancer cells ($2 \times 10^5$ in 50 µl) were then plated on the filters in each of the top chambers. Compound 1 or uridine was diluted in the serum-free medium to 0.536 mg/ml and then was added to the top chambers, with the volume of 50 µl/chamber. The control tests were performed with 2 µM paclitaxel (positive control) or with medium only (negative control) in the top chambers.

After an 18-hour incubation, the cells in the top chambers were carefully emptied with sterile cotton buds. 100 µl XTT reagent (1 mg/ml) was added to each of the bottom wells. After incubating for 4 hours, absorbance (O.D.) was measured at 450 nm with the reference wavelength at 690 nm. The ratio of the OD from the bottom wells to that of the OD from the bottom wells of the control tests was taken as the invasive potential. Results presented are from three different independent experiments.

Figure 5:
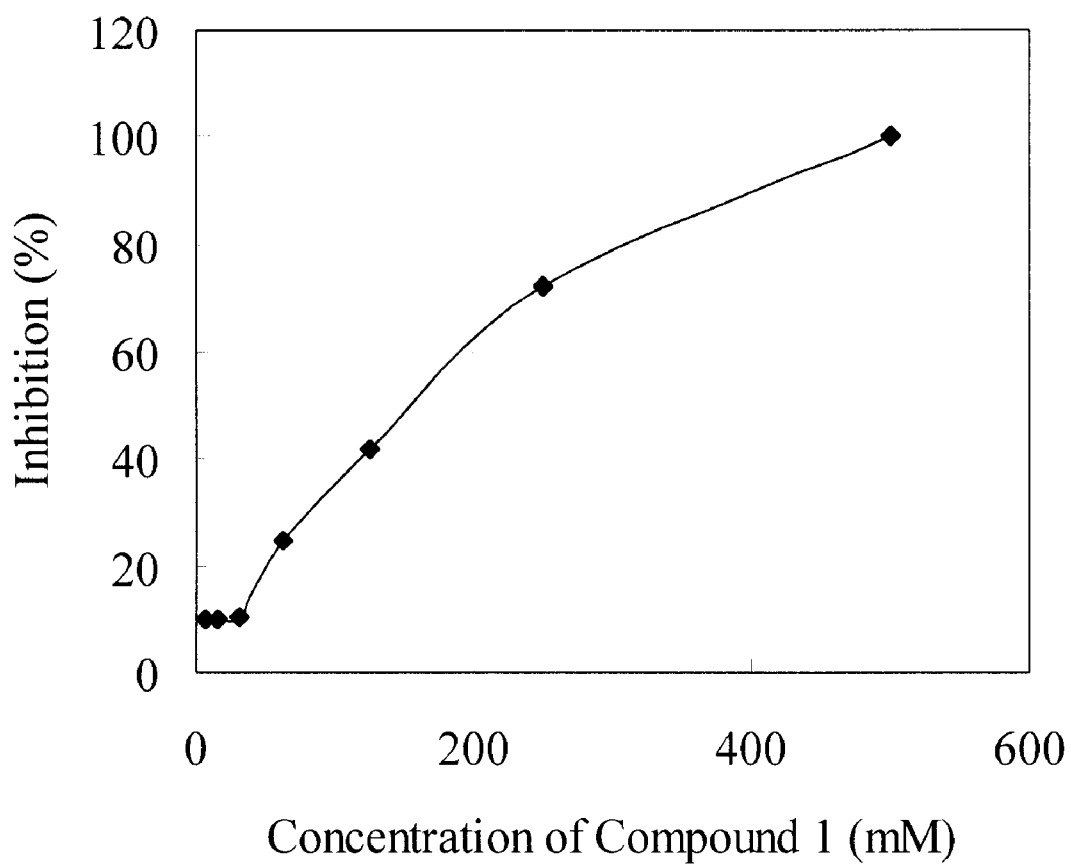
FIG. 5 shows the inhibition of invasive potential of ES-2 cells by Compound 1.

The effect of Compound 1 on the invasive potential on ES-2 cell lines was shown in FIG. 5. The ability of Compound 1 to inhibit invasive activity varied significantly from cell line to cell line. ES-2 was the most affected cell line. In particular, the 50% inhibitory dose (IC50) was 23 µg/ml (i.e. 0.09 µM). The other four cell lines were not significantly affected by Compound 1 in the same ranges as ES-2 (data not shown). As for uridine, it did not show any effect on all the five cancer cell lines in this experiment (data not shown).

Structure-Activity Relationship on Inhibiting MMP-2 of Compound 1

Peter D, Brown et al. and G. Clemens et al. have discussed about the structure-activity relationships of several matrix metaloproteinase inhibitors (MMPIs) such as hydroxamic acid and 4-biphenoyl propionic acid (Clendeninn, NJ and Appelt K (2001) Matrix Metallopoteinase inhibtiors in Cancer Therapy. Humana Press Inc. NJ) (Chapter 5. pp.113–142; Chapter 7, pp.175–192). The requirements for a molecule to be an effective inhibitor of the MMPs are a functional group (e.g., carboxylic acid, hydroxamic acid, and sulfhydryl, etc.) capable of chelating the zinc (II) ion of the active site, at least one functional group which provides a hydrogen bond interaction with the enzyme back-bone and one or more side chains which undergo effective Van der Waals interactions with the enzyme subsites.

Comparing the structure of Compound 1 with the requirements described above, it was shown that the hydroxy group on the hydroxyethyl part of Compound 1 should be responsible for the chelating of the Zn (II) ion in the active site of MMP-2 enzyme. The pyrimidine part of Compound 1 can offer Van der Waals interaction with the enzyme subsites, and the oxygen and nitrogen atoms of compound 1 can form hydrogen-bondings to the MMP-2's peptide back-bone.

Therefore, it is reasonable to replace the hydroxyethyl ($CH_2CH_2OH$) part of Compound 1 to other functional groups capable of chelating Zn (II) ion in the active site of the MMP-2 enzyme. The other chelating functional groups can be, for example, $(CH_2)_nOH$, $(CH_2)_nNH_2$, $(CH_2)_nSH$, $(CH_2)_mCOOH$, $(CH_2)_mCOOR$, $(CH_2)_mCONH_2$, $(CH_2)_{m''}CONH-OH$, $(CH_2)_{m''}CONH-R$, and $(CH^2)_{n'}O(PO_3)_{m''}{}^{(m''+1)}$, wherein n=2,3,4, or 5, n'=2 or 3, m=1, 2, 3, or 4, m'=1, 2, 3, 4, 5, or 6, m''=1, 2, 3, and R=—$C_mH_{2m'+1}$ or aryl groups.

Inhibitory Effect of Compound 1 on TNFα Binding To TNFα-RI

50 μl TNFα-RI at a concentration of 0.25 μg/ml was coated onto each well of a 96-well C-bottom microtiter plate (Nunc) in a 50 mM carbonate buffer (pH 9.5) at 4° C. overnight. The plate was washed 3 times with 200 μl TBST solution composed of 50 mM Tris.HCl (pH 7.35) containing 0.15 M NaCl and 0.05% Tween 20 to remove excess TNFα-RI. 200 μl/well of 0.5% BSA in PBS was added to each plate for blocking of the TNFα-RI. The reaction was carried out at 37° C. for 2 hours followed by washing 4 times with TBST to remove excess BSA.

Compound 1 was serially diluted in TBST solution. Biotinylated TNFα with a concentration of 0.5 μg/ml was mixed with Compound 1 solution in a volume ratio of 1:1. The reaction was allowed to proceed for 30 minutes at 37° C. with shaking at 500 rpm for allowing mixing. The mixtures were then added to the TNFα-RI coated plate, 50 μl for each well. The plate was then incubated at 37° C. for 2 hours with shaking again at 500 rpm, for competitive binding of the biotinylated TNFα and Compound 1.

Followed by washing 4 times with TBST, Extravidin-alkaline phosphatase (Sigma) diluted in TBST (1/5,000) was added to the plate, 50 μl/well. The plate was further incubated at 37° C. for 2 hours and then washed 4 times with TBST. A substrate of alkaline phosphatase, p-nitrophenyl phosphate, at a concentration of 1 mg/ml in 50 mM carbonate buffer (pH 9.5) containing 5 mM $MgCl_2$ was added to the plate, 50 μl/well. After a 30-minute incubation at room temperature, absorbance at the wavelength of 405 nm was measured. Suramin, a known inhibitor of TNFα binding to TNFα-RI, was used as a control and comparative compound in this experiment.

Figure 6:
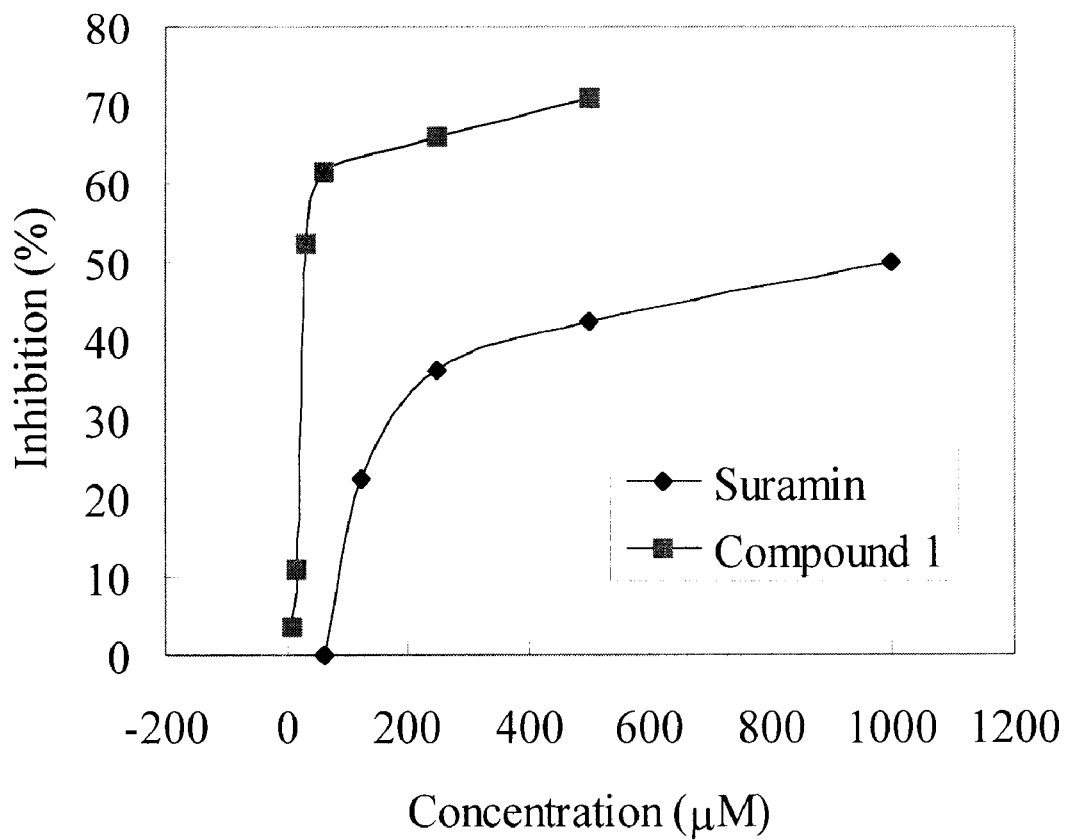
FIG. 6 shows the inhibitory effect of Compound 1 on the binding activity of biotinylated TNFα to TNFα-RI.

FIG. 6 shows the inhibitory effect of Compound 1 on the binding activity of biotinylated TNFα to TNFα-RI. Each data point represented the mean value of a triplicate measurement. Suramin was used for comparison in the experiment. The result in FIG. 6 showed that the inhibition percentage was increased as the compound 1 concentration increases, although the inhibition activity is smaller than that of Suramin. Therefore, compound 1 has an inhibitory activity on TNFα binding to TNFα-RI. The 50% inhibitory dose (IC50) was 50 μM.

As discussion above, Compound 1 has an inhibitory effect on MMP-2 and on the binding of TNFα to TNFα-RI. The derivatives of Compound 1, as discussed in the section, STRUCTURE-ACTIVITY RELATIONSHIP OF INHIBITING MMP-2 BY COMPOUND 1, also have an inhibitory effect on MMP-2.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method to treat TNFα-related disorders in a mammal in need thereof, comprising administering an inhibitor of TNFα binding to TNFα-RI receptor in a therapeutically effective amount to said mammal, wherein said inhibitor is 1-[3,4-dihydroxy-5-(2-hydroxyethyl)tetrahydrofuran-2-yl] pyrimidine-2,4(1H,3H)-dione.

2. The method of claim 1, wherein said disorder is ovarian carcinoma.

3. The method of claim 1, wherein said mammal is human.

4. The method of claim 1, further comprising the simultaneous treatment of MMPs-related disorders in a mammal in need thereof.

5. The method of claim 1, wherein said inhibitor is a pharmaceutical composition, comprising an effective amount of said inhibitor in admixture with a suitable pharmaceutical excipient.

* * * * *